United States Patent
Mu et al.

(10) Patent No.: US 11,131,623 B2
(45) Date of Patent: Sep. 28, 2021

(54) MIXTURE DETECTION METHOD AND DEVICE

(71) Applicant: CloudMinds (Shenzhen) Holdings Co., Ltd., Guangdong (CN)

(72) Inventors: Taotao Mu, Beijing (CN); Lei Luo, Beijing (CN)

(73) Assignee: CLOUDMINDS (SHENZHEN) HOLDINGS CO., LTD., Guangdong (CN)

( * ) Notice: Subject to any disclaimer, the term of this patent is extended or adjusted under 35 U.S.C. 154(b) by 303 days.

(21) Appl. No.: 16/328,512

(22) PCT Filed: Nov. 28, 2017

(86) PCT No.: PCT/CN2017/113420
§ 371 (c)(1),
(2) Date: Feb. 26, 2019

(87) PCT Pub. No.: WO2019/104489
PCT Pub. Date: Jun. 6, 2019

(65) Prior Publication Data
US 2021/0109013 A1 Apr. 15, 2021

(51) Int. Cl.
G01J 3/44 (2006.01)
G01N 21/27 (2006.01)
(Continued)

(52) U.S. Cl.
CPC ....... G01N 21/274 (2013.01); G06K 9/00543 (2013.01); G16C 20/10 (2019.02); *G01N 2201/1293* (2013.01)

(58) Field of Classification Search
CPC .... G01N 21/3504; G01N 21/65; G01N 30/02; G01N 21/031; G01N 21/85; G01N 33/004; G06F 16/245; G01J 3/26; G01J 3/42
See application file for complete search history.

(56) References Cited

U.S. PATENT DOCUMENTS

2011/0165586 A1 7/2011 Kim et al.

FOREIGN PATENT DOCUMENTS

| CN | 101419159 A | 4/2009 |
| CN | 103234952 A | 7/2013 |
| | (Continued) | |

OTHER PUBLICATIONS

Translation of CN105223184A (Year: 2016).*
(Continued)

*Primary Examiner* — David P Porta
*Assistant Examiner* — Mamadou Faye
(74) *Attorney, Agent, or Firm* — Dilworth IP, LLC (57) ABSTRACT

A mixture detection method and device relating to substance detection technology. The proportion contents of substances contained in a mixture can be detected. The method includes: performing measurement spectrum line collection on a to-be-detected mixture to identify the kinds of substances in the to-be-detected mixture; selecting a characteristic peak of a measurement spectrum line of each kind of substance according to the kinds of substances, and obtaining an intensity proportion of the characteristic peak of each kind of substance; querying a relative activity database according to the kinds of the substances to obtain relative activity corresponding to each kind of substance; and determining the proportion contents of the substances contained in the mixture according to the intensity proportion of the characteristic peak of each kind of substance and the quotient of the relative activities.

10 Claims, 3 Drawing Sheets

(51) Int. Cl.
　　　　*G16C 20/10*　　　　(2019.01)
　　　　*G06K 9/00*　　　　(2006.01)

(56) References Cited

FOREIGN PATENT DOCUMENTS

| CN | 103439310 | A | | 11/2013 |
|---|---|---|---|---|
| CN | 103424395 | A | | 12/2013 |
| CN | 103529013 | A | | 1/2014 |
| CN | 104198517 | A | | 12/2014 |
| CN | 105223184 | A | * | 1/2016 |
| CN | 106732544 | A | | 5/2017 |
| EP | 2320216 | A2 | | 5/2011 |
| JP | 2005106698 | A | | 4/2005 |

OTHER PUBLICATIONS

Cleveland et al., (2007), "Raman Spectroscopy for the Undergraduate Teaching Laboratory: Quantification of Ethanol Concentration in Consumer Alcoholic Beverages and Qualitative Identification of Marine Diesels Using a Miniature Raman Spectrometer". Spectrosc Lett. 40. 903-924.
Extended European Search Report, Application No. 17928821.2, dated Nov. 25, 2019, 12 pages.
PCT International Search Report dated Aug. 22, 2018 in corresponding Application No. PCT/CN2017/113420, 6 pages.
Written Opinion of the International Searching Authority dated Aug. 22, 2018 in corresponding Application No. PCT/CN2017/113420, 7 pages.
Chinese Search Report from corresponding Chinese Application No. CN201780002742.X dated May 17, 2021, 7 pages.

\* cited by examiner

MIXTURE DETECTION METHOD AND DEVICE

CROSS-REFERENCE TO RELATED APPLICATION

This application claims the benefit of PCT application No. PCT/CN2017/113420 filed on Nov. 28, 2017, the contents of which are incorporated herein by reference.

FIELD OF THE INVENTION

The embodiment of the present invention relates to substance detection technology, and more particularly to a mixture detection method and device.

BACKGROUND OF THE INVENTION

During substance detection, the detection by instrumental analysis at present is mainly based on the comparison of substance characteristics stored in databases, such as the comparison of the spectral characteristics of the substances. The volume is great when the database is constructed based on the mixture. For example, if the mixture database is constructed by using the original method, the data size is very large. If every two of 10,000 substances are mixed, there are 49,995,000 possibilities. If every three are mixed, there are $1.67*10^{11}$ possibilities. If different mixing proportions are considered, the types will increase by 100 times. These make the solution unfeasible. Therefore, the constructed database is mainly a single pure substance database, which can only satisfy the analysis and identification of a single substance. Moreover, by using the method, only the kinds of the substances can be identified, but the proportion contents of the substances contained in the mixture cannot be detected.

SUMMARY OF THE INVENTION

The embodiment of the present invention provides a mixture detection method and device capable of detecting the proportion contents of substances contained in a mixture.

In a first aspect, a mixture detection method is provided, including:

performing measurement spectrum line collection on a mixture to identify the kinds of substances in the mixture, wherein the solvent of the mixture is a first calibration substance;

selecting a characteristic peak of a measurement spectrum line of each kind of substance according to the kinds of substances, and obtaining an intensity proportion of the characteristic peak of each kind of substance;

querying a relative activity database according to the kinds of the substances to obtain relative activity corresponding to each kind of substance, wherein the relative activity database includes the relative activity L of at least one kind of standard sample substance, wherein $$L = C\sum_{i=0}^{n} L(i)/n,$$

$L(i)=I(i)/(T*W)$, and C is a constant; and when the first calibration substance is mixed with the standard sample substance according to a first predetermined proportion, T represents an integration time when the characteristic peak of the measurement spectrum line of the standard sample substance reaches an intensity value I(i), W represents the excitation intensity of a signal source of the measurement spectrum line, and n represents the collection times of the intensity value of the measurement spectrum line of the standard sample substance; and determining the proportion contents of the substances contained in the mixture according to the intensity proportion of the characteristic peak of each kind of substance and a product of the relative activities.

In a second aspect, a mixture detection device is provided, including:

a detection unit, configured to perform measurement spectrum line collection on a mixture to identify the kinds of substances in the mixture, wherein the solvent of the mixture is a first calibration substance; and a processing unit, configured to select a characteristic peak of a measurement spectrum line of each kind of substance according to the kinds of substances identified by the detection unit, and obtaining an intensity proportion of the characteristic peak of each kind of substance;

wherein the processing unit is configured to query a relative activity database according to the kinds of the substances identified by the detection unit to obtain relative activity corresponding to each kind of substance, wherein the relative activity database includes the relative activity L of at least one kind of standard sample substance, wherein $$L = C\sum_{i=0}^{n} L(i)/n,$$

$L(i)=I(i)/(T*W)$, and C is a constant; and when the first calibration substance is mixed with the standard sample substance according to a first predetermined proportion, T represents an integration time when the characteristic peak of the measurement spectrum line of the standard sample substance reaches an intensity value I(i), W represents the excitation intensity of a signal source of the measurement spectrum line, and n represents the collection times of the intensity value of the measurement spectrum line of the standard sample substance; and the processing unit is further configured to determine the proportion contents of the substances contained in the mixture according to the intensity proportion of the characteristic peak of each kind of substance and a product of the relative activities.

In a third aspect, a mixture detection device is provided, including: a memory, an interface and a processor; the memory and a communication interface are coupled to the processor; and the memory is configured to store computer executable codes, the processor is configured to execute the computer executable codes to control the execution of the mixture detection method of the first aspect, and the interface is configured for data transmission of the mixture detection device and an external device.

In a fourth aspect, a computer readable storage medium storing one or more programs is provided, the one or more programs include instructions, and the instructions cause a computer to execute the mixture detection method of the first aspect when being executed by the computer.

In the above solutions, firstly, the measurement spectrum line collection is performed on the mixture to identify the kinds of substances in the mixture, and the solvent of the mixture is the first calibration substance; then, the characteristic peak of the measurement spectrum line of each kind of substance is selected according to the kinds of substances, and the intensity proportion of the characteristic peak of each kind of substance is obtained; the relative activity database is queried according to the kinds of the substances to obtain the relative activity corresponding to each kind of substance, wherein the relative activity database includes the relative activity L of at least one kind of standard sample substance, wherein $$L = C\sum_{i=0}^{n} L(i)/n,$$

$L(i)=I(i)/(T*W)$, and C is a constant; and when the first calibration substance is mixed with the standard sample substance according to the first predetermined proportion, T represents an integration time when the characteristic peak of the measurement spectrum line of the standard sample substance reaches an intensity value I(i), W represents the excitation intensity of a signal source of the measurement spectrum line, and n represents the collection times of the intensity value of the measurement spectrum line of the standard sample substance; and the proportion contents of the substances contained in the mixture are determined according to the intensity proportion of the characteristic peak of each kind of substance and the product of the relative activities. Therefore, the proportion contents of the substances contained in the mixture are detected.

BRIEF DESCRIPTION OF THE DRAWINGS

To illustrate technical solutions in the embodiments of the present invention more clearly, a brief introduction on the accompanying drawings which are needed in the description of the embodiments or the prior art is given below. Apparently, the accompanying drawings in the description below are merely some of the embodiments of the present invention, based on which other accompanying drawings can be obtained by those of ordinary skill in the art without any creative effort.

DETAILED DESCRIPTION OF THE EMBODIMENTS

It should be noted that, in the embodiment of the present invention, the words "exemplary" or "for example" and the like are used as examples, illustrations or descriptions. Any embodiment or design solution described as "exemplary" or "for example" in the embodiment of the present invention should not be construed as preferred or more advantageous over other embodiments or designs. Exactly, the words "exemplary" or "for example" and the like are used for presenting related concepts in a specific manner.

It should be noted that, in the embodiment of the present invention, "of", "relevant" and "corresponding" can sometimes be used interchangeably. It should be noted that, when the difference is not emphasized, the meanings to be expressed are the same.

The mixture detection device provided by the embodiment of the present invention is a PC or the like installed with a software client or a software system or a software application that can execute the method provided by the embodiment of the present invention, and the specific hardware implementation environment can be a general-purpose computer form, or an ASIC manner, or FPGA, or some programmable extension platforms such as an Xtensa platform of Tensilica and so on. The basic components include a processor, a hard disk, a memory, a system bus and the like, which are similar to the general-purpose computer architecture.

Figure 1:
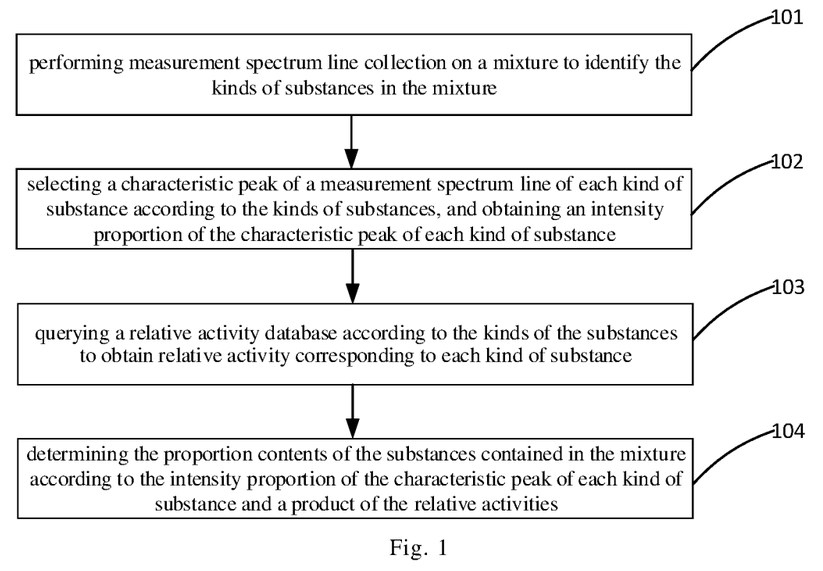
FIG. 1 is a flowchart of a mixture detection method provided by an embodiment of the present invention.

Based on the above-mentioned mixture detection device, as shown in FIG. 1, the embodiment of the present invention provides a mixture detection method, including the following steps:

101, measurement spectrum line collection is performed on a mixture to identify the kinds of substances in the mixture, wherein the solvent of the mixture is a first calibration substance.

102, a characteristic peak of a measurement spectrum line of each kind of substance is selected according to the kinds of substances, and an intensity proportion of the characteristic peak of each kind of substance is obtained.

103, a relative activity database is queried according to the kinds of the substances to obtain relative activity corresponding to each kind of substance.

Wherein the relative activity database includes the relative activity L of at least one kind of standard sample substance.

$$L = C\sum_{i=0}^{n} L(i)/n,$$

$L(i)=I(i)/(T*W)$, and C is a constant; and when the first calibration substance is mixed with the standard sample substance according to a first predetermined proportion, T represents an integration time when the characteristic peak of the measurement spectrum line of the standard sample substance reaches an intensity value I(i), W represents the excitation intensity of a signal source of the measurement spectrum line, and n represents the collection times of the intensity value of the measurement spectrum line of the standard sample substance. Wherein the standard sample substance is mixed with the first calibration substance in equal proportions, the measurement spectrum line includes at least one of the following: Raman spectrum, infrared spectrum, laser induced breakdown spectrum LIBS, mass spectrum, chromatography, and ionic migration spectrum; and n is at least one, and is 3-5 in a preferred example.

104, the proportion contents of the substances contained in the mixture are determined according to the intensity proportion of the characteristic peak of each kind of substance and a product of the relative activities.

In the above solution, firstly, the measurement spectrum line collection is performed on the mixture to identify the kinds of substances in the mixture, and the solvent of the mixture is the first calibration substance; then, the characteristic peak of the measurement spectrum line of each kind of substance is selected according to the kinds of substances, and the intensity proportion of the characteristic peak of each kind of substance is obtained; the relative activity database is queried according to the kinds of the substances to obtain the relative activity corresponding to each kind of substance, wherein the relative activity database includes the relative activity L of at least one kind of standard sample substance, wherein $$L = C\sum_{i=0}^{n} L(i)/n,$$

$L(i)=I(i)/(T*W)$, and C is a constant; and when the first calibration substance is mixed with the standard sample substance according to the first predetermined proportion, T represents an integration time when the characteristic peak of the measurement spectrum line of the standard sample substance reaches an intensity value I(i), W represents the excitation intensity of a signal source of the measurement spectrum line, and n represents the collection times of the intensity value of the measurement spectrum line of the standard sample substance; and the proportion contents of the substances contained in the mixture are determined according to the intensity proportion of the characteristic peak of each kind of substance and the product of the relative activities. Therefore, the proportion contents of the substances contained in the mixture are detected.

Figure 2:
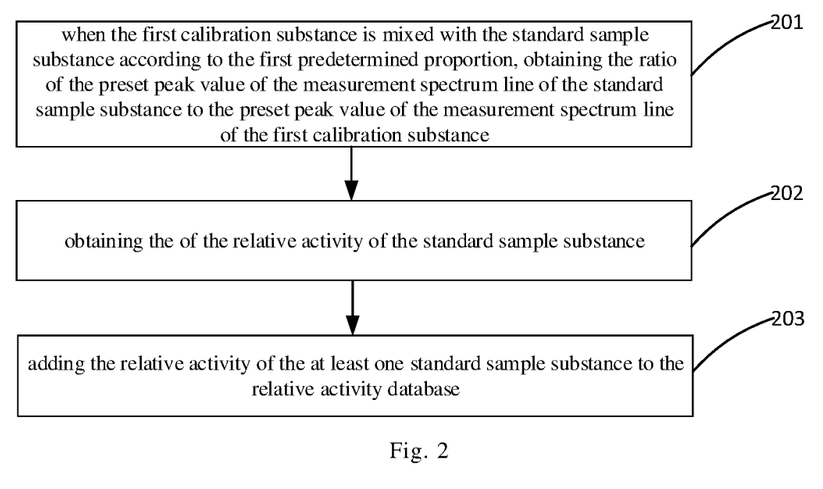
FIG. 2 is a flowchart of a mixture detection method provided by another embodiment of the present invention.

Before the step 101, the relative activity database needs to be constructed. As shown in FIG. 2, the method includes the following steps:

201, when the first calibration substance and the standard sample substance are mixed according to a first predetermined proportion, the excitation intensity W of the signal source is set, and the integration time T is set.

202, the relative activity L of the standard sample substance is obtained, when the characteristic peak of the measurement spectrum line of the standard sample substance reaches the intensity value I(i).

203, the relative activity L of at least one standard sample substance is added to the relative activity database.

It should be noted that, when the standard sample substances are different, the solvents (the first calibration substances) capable of dissolving the same are also different, therefore, in order to perform unified calculation, the relative activities can be converted into a unified relative activity with reference to a second calibration substance. For example, if a part of substances in the relative active database is soluble in water, a part of substances are soluble in ethanol, then the relative activities L of the substances soluble in water can be directly calculated, and the constant is set as C=1. The value of the constant C of the substances soluble in ethanol can be calculated according to the following method:

When the first calibration substance and the second calibration substance are mixed according to a second proportion, the excitation intensity W of the signal source is set, and the integration time T is set; the relative activity $$L_1 = \sum_{i=0}^{n} L_1(i)/n,$$

$L_1(i)=I_1(i)/(T*W)$ of the first calibration substance is obtained, when the characteristic peak of the measurement spectrum line of the first calibration substance reaches the intensity value $I_1(i)$; the relative activity $$L_2 = \sum_{i=0}^{n} L_2(i)/n,$$

$L_2(i)=I_2(i)/(T*W)$ of the first calibration substance is obtained, when the characteristic peak of the measurement spectrum line of the second calibration substance reaches the intensity value $I_2(i)$; and the constant $C=L_1\backslash L_2$ is calculated. After ethanol and water are mixed, the ratio of the relative activity $L_{alcohol}$ of the ethanol to the relative activity $L_{water}$ of water is set as C. Based on the above method, the relative activity L can be converted to the unified reference calibration substance, so that the subsequent calculation of the proportion contents of the substances contained in the mixture is not affected. Of course, the above descriptions are merely illustrations by using the ethanol and water as the calibration substances. When other substances are used as the calibration substances, the calculation method of the constant a is similar, and will not be described again.

Figure 3:
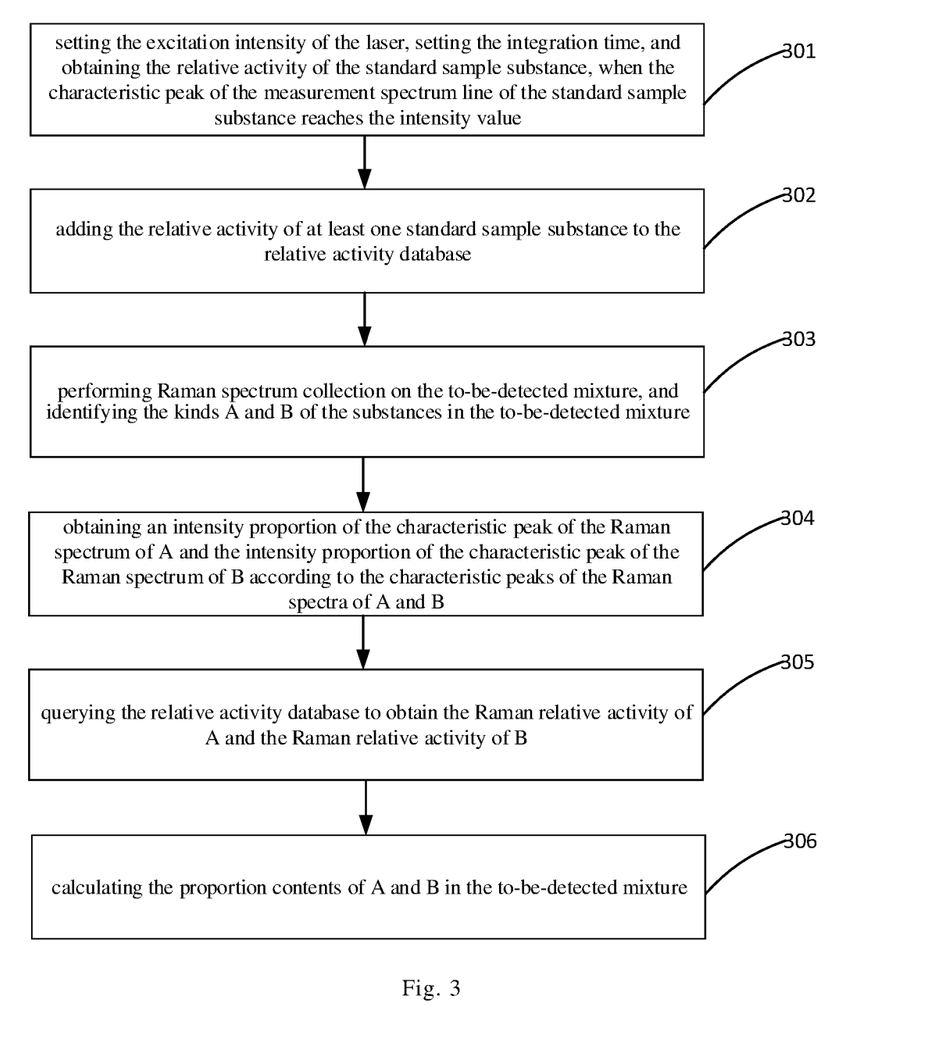
FIG. 3 is a flowchart of a mixture detection method provided by yet another embodiment of the present invention.

Exemplarily, using an example that the measurement spectrum line is the Raman spectrum, the signal source is a laser, the to-be-detected mixture is a mixture of substances A and B, and the detection method thereof, as shown in FIG. 3, is specifically as follows:

301, the excitation intensity W of the laser is set, the integration time T is set, and the relative activity L of the standard sample substance is obtained, when the characteristic peak of the measurement spectrum line of the standard sample substance reaches the intensity value I(i).

Exemplarily, the value range of the integration time T is generally 0.1-10 seconds, the excitation intensity is 350 mW, the intensity value of the characteristic peak of the Raman spectrum of the standard sample substance can be collected for 3-5 times, and then averaging is performed to obtain the relative activity $$L = C\sum_{i=0}^{n} L(i)/n,$$

of the standard sample substance. For the value of C herein, reference can be made to the above method and it is not described again.

302, the relative activity L of at least one standard sample substance is added to the relative activity database.

The relative activity of each substance is obtained by analogy via the steps 301-302, and the relative activity database is established.

303, Raman spectrum collection is performed on the to-be-detected mixture, and the kinds A and B of the substances in the to-be-detected mixture are identified.

304, an intensity proportion $C_A$ of the characteristic peak of the Raman spectrum of A and the intensity proportion $C_B$ of the characteristic peak of the Raman spectrum of B are obtained according to the characteristic peaks of the Raman spectra of A and B.

305, the relative activity database is queried to obtain the Raman relative activity $L_A$ of A and the Raman relative activity $L_B$ of B.

306, the proportion contents of A and B in the to-be-detected mixture are calculated as: $(C_A/L_A):(C_B/L_B)$.

The above descriptions are merely illustrations by taking the mixture of two substances as an example, a plurality of mixtures can be sequentially calculated according to the method, the above analysis process of the proportion of the mixture can be applied to joint detection scenarios such as non-destructive detection reaction degree of a chemical reaction process, reaction completion degree in a substance synthesis process such as drugs and fertilizers and the like.

The embodiment of the present invention can divide the function modules of the mixture detection device according to the above method example. For example, the function modules can be divided according to the functions, and two or more functions can also be integrated into one processing module. The above integrated modules can be implemented in the form of hardware or in the form of software functional modules. It should be noted that, the division of the modules in the embodiment of the present invention is schematic and is only a logical function division, and there may be other division manners in the actual implementation.

Figure 4:
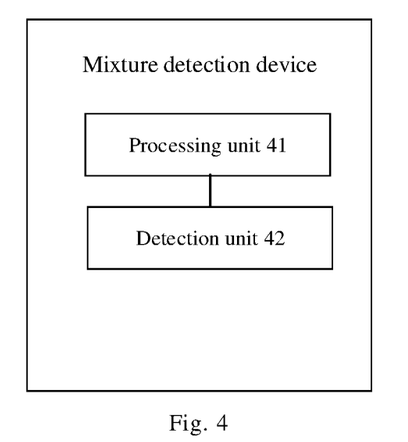
FIG. 4 is a structural schematic diagram of a mixture detection device provided by an embodiment of the present invention.

An example is provided, FIG. 4 shows a possible structural schematic diagram of the mixture detection device provided involved in the embodiment of the present invention, and the mixture detection device includes a processing unit 41 and a detection unit 42. The processing unit 41 is configured to support the mixture detection device to execute the processes 102, 103 and 104 in FIG. 1; and the detection unit 42 is configured to support the mixture detection device to execute the process 101 in FIG. 1. All related contents in the steps involved in the above method embodiment can be quoted to the function descriptions of the corresponding functional modules, for example, it is not repeated redundantly herein.

Figure 5A:
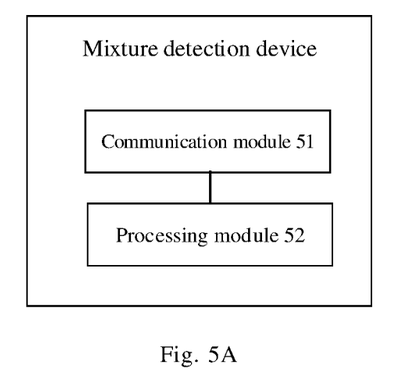
FIG. 5A is a structural schematic diagram of a mixture detection device provided by another embodiment of the present invention.

Another example is provided, FIG. 5A show a possible structural schematic diagram of the mixture detection device provided involved in the embodiment of the present invention. The mixture detection device includes a communication module 51 and a processing module 52. The processing module 52 is configured to control and managing the actions of the mixture detection device, for example, the processing module 52 is configured to support the mixture detection device to execute the processes 101-104 in FIG. 1. The communication module 51 is configured to support the mixture detection device to perform data transmission with other external devices, such as the communication with a sensor, to obtain a collection result of the sensor on a measurement spectrum line. The mixture detection device can further include a storage module for storing program codes and data of the mixture detection device.

The processing module 52 can be a processor or a controller, for example, can be a central processing unit (CPU), a general-purpose processor, a digital signal processor (DSP), an application-specific integrated circuit (ASIC), a field programmable gate array (FPGA) or other programmable logic device, a transistor logic device, a hardware component, or any combination thereof. The processing module can implement or execute various illustrative logical blocks, modules and circuits described in combination with the contents disclosed in the present invention. The processor can also be a combination for achieving computing functions, such as a combination of one or more microprocessors, a combination of a DSP and a microprocessor, or the like. The communication module 81 can be a transceiver, a transceiver circuit, a communication interface or the like. The storage module can be a memory.

Figure 5B:
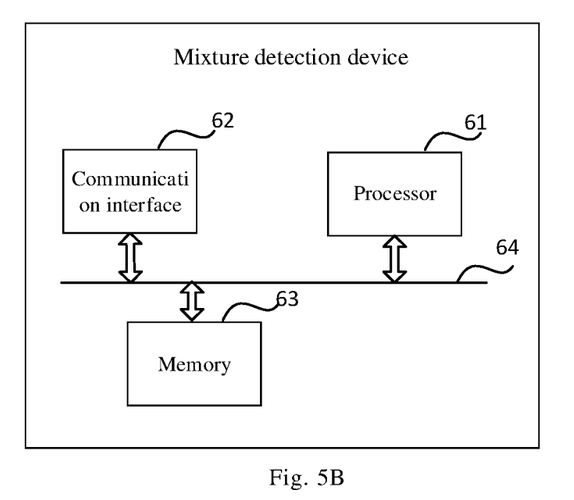
FIG. 5B is a structural schematic diagram of a mixture detection device provided by yet another embodiment of the present invention.

Exemplarily, the processing module 52 can be a processor, the communication module 51 can be a communication interface, and the storage module can be a memory. As shown in FIG. 5B, a mixture detection device is provided, including: a processor 61, a communication interface 62, a memory 63 and a bus 64; the memory 63 and the communication interface 62 are coupled to the processor 61 via the bus 64; and the bus 64 can be a peripheral component interconnect (PCI) bus or an extended industry standard architecture (EISA) bus or the like. The bus can be divided into an address bus, a data bus, a control bus, and the like. For ease of representation, the bus is just expressed by a thick line in FIG. 6B; however, it does not mean that there is only one bus or one type of buses.

The embodiment of the present invention further provides a computer readable storage medium storing one or more programs, wherein the one or more programs include instructions, and the instructions cause a computer to execute the mixture detection method of the above embodiment when being executed by the computer.

The embodiment of the present invention further provides a computer program product that can be directly loaded into an internal memory of a computer and contains software codes, and the computer program can be loaded and executed by the computer to implement the mixture detection method provided by the above embodiment.

The steps of the method or algorithm described in combination with the disclosed contents of the present invention can be implemented in a hardware form, or can be implemented by a processor executing software instructions. The software instructions can be composed of corresponding software modules, and the software modules can be stored in a random access memory (RAM), a flash memory, a read only memory (ROM), an erasable programmable read only memory (EPROM), an electrically erasable programmable read only memory (EEPROM), a register, a hard disk, a mobile hard disk, a compact disk read only (CD-ROM) or any other form of storage medium known in the art. An exemplary storage medium is coupled to the processor, so that the processor can read information from the storage medium and can write information into the storage medium. Of course, the storage medium can also be a constituent part of the processor. The processor and the storage medium can be located in an ASIC. Additionally, the ASIC can be located in a core network interface device. Of course, the processor and the storage medium can also exist as discrete components in the core network interface device.

Those skilled in the art will appreciate that, in one or more examples described above, the functions described by the present invention can be implemented by hardware, software, firmware, or any combination thereof. When implemented by the software, these functions can be stored in a computer readable medium or transmitted as one or more instructions or codes on the computer readable medium. The computer readable media includes a computer storage medium and a communication medium, wherein the communication medium includes any medium that is convenient for transmitting a computer program from one location to another. The storage medium can be any available medium that can be accessed by a general purpose or special purpose computer.

The objectives, the technical solutions and the beneficial effects of the present invention are further described in detail in the above specific embodiments. It should be understood that the foregoing descriptions are only exemplary embodiments of the present invention and are not intended to limit the present invention, and any modifications, equivalent substitutions, improvements and the like made on the basis of the technical solutions of the present invention should be included in the protection scope of the present invention.

The invention claimed is:

1. A mixture detection method, comprising:
performing measurement spectrum line collection on a mixture consisting of different kinds of substances to identify the kinds of the substances in the mixture, wherein a solvent of the mixture is a first calibration substance;
selecting a characteristic peak of a measurement spectrum line of each kind of substance according to the kinds of the substances, and obtaining an intensity proportion of the characteristic peak of each kind of substance;
querying a relative activity database according to the kinds of the substances to obtain relative activity corresponding to each kind of substance, wherein the relative activity database comprises the relative activity L of at least one kind of standard sample substance, wherein $$L = C \sum_{i=0}^{n} L(i)/n,$$

$L(i)=I(i)/(T*W)$, and C is a constant; and when the first calibration substance is mixed with the standard sample substance according to a first predetermined proportion, T represents an integration time when the characteristic peak of the measurement spectrum line of the standard sample substance reaches an intensity value I(i), W represents an excitation intensity of a signal source of the measurement spectrum line, and n represents collection times of the intensity value of the measurement spectrum line of the standard sample substance; and
determining the proportion contents of the different kinds of substances contained in the mixture according to the intensity proportion of the characteristic peak of each kind of substance and a quotient of the relative activities.

2. The method according to claim 1, further comprising:
when the first calibration substance and the standard sample substance are mixed according to a first predetermined proportion, setting the excitation intensity W of the signal source, and setting the integration time T;
obtaining the relative activity L of the standard sample substance, when the characteristic peak of the measurement spectrum line of the standard sample substance reaches the intensity value I(i); and
adding the relative activity L of at least one standard sample substance to the relative activity database.

3. The method according to claim 1, further comprising:
when the first calibration substance and the standard sample substance are mixed according to a second predetermined proportion, setting the excitation intensity W of the signal source, and setting the integration time T;
obtaining the relative activity $$L_1 = \sum_{i=0}^{n} L_1(i)/n,$$

$L_1(i)=I_1(i)/(T*W)$ of the first calibration substance, when the characteristic peak of the measurement spectrum line of the first calibration substance reaches the intensity value $I_1(i)$; and the relative activity $$L_2 = \sum_{i=0}^{n} L_2(i)/n,$$

$L_2(i)=I_2(i)/(T*W)$ of the first calibration substance, when the characteristic peak of the measurement spectrum line of a second calibration substance reaches the intensity value $I_2(i)$; and
calculating the constant $C=L_1 \backslash L_2$.

4. The method according to claim 1, wherein the standard sample substance is mixed with the first calibration substance in equal proportions.

5. The method according to claim 1, wherein the measurement spectrum line comprises at least one of the following: Raman spectrum, infrared spectrum, laser induced breakdown spectrum LIBS, mass spectrum, chromatography, and ionic migration spectrum.

6. A mixture detection device, comprising: a memory, an interface and a processor; the memory and a communication interface are coupled to the processor; the memory is configured to store computer executable instructions, the interface is configured for data transmission of the mixture detection device and an external device, and the processor is configured to execute the computer executable instructions to control an execution of a mixture detection method comprising:
performing measurement spectrum line collection on a mixture consisting of different kinds of substances to identify the kinds of the substances in the mixture, wherein a solvent of the mixture is a first calibration substance;
selecting a characteristic peak of a measurement spectrum line of each kind of substance according to the kinds of the substances, and obtaining an intensity proportion of the characteristic peak of each kind of substance;
querying a relative activity database according to the kinds of the substances to obtain relative activity corresponding to each kind of substance, wherein the relative activity database comprises the relative activity L of at least one kind of standard sample substance, wherein $$L = C \sum_{i=0}^{n} L(i)/n,$$

$L(i)=I(i)/(T*W)$, and C is a constant; and when the first calibration substance is mixed with the standard sample substance according to a first predetermined proportion, T represents an integration time when the characteristic peak of the measurement spectrum line of the standard sample substance reaches an intensity value I(i), W represents an excitation intensity of a signal source of the measurement spectrum line, and n represents collection times of the intensity value of the measurement spectrum line of the standard sample substance; and
determining the proportion contents of the different kinds of substances contained in the mixture according to the intensity proportion of the characteristic peak of each kind of substance and a quotient of the relative activities.

7. The mixture detection device according to claim 6, wherein the processor is further configured to execute the computer executable instructions to implement the following steps:
when the first calibration substance and the standard sample substance are mixed according to a first predetermined proportion, setting the excitation intensity W of the signal source, and setting the integration time T;
obtaining the relative activity L of the standard sample substance, when the characteristic peak of the measurement spectrum line of the standard sample substance reaches the intensity value I(i); and
adding the relative activity L of at least one standard sample substance to the relative activity database.

8. The mixture detection device according to claim 6, wherein the processor is further configured to execute the computer executable instructions to implement the following steps:
when the first calibration substance and the standard sample substance are mixed according to a second predetermined proportion, setting the excitation intensity W of the signal source, and setting the integration time T;
obtaining the relative activity $$L_1 = \sum_{i=0}^{n} L_1(i)/n,$$

$L_1(i)=I_1(i)/(T^*W)$ of the first calibration substance, when the characteristic peak of the measurement spectrum line of the first calibration substance reaches the intensity value $I_1(i)$; and the relative activity $$L_2 = \sum_{i=0}^{n} L_2(i)/n,$$

$L_2(i)=I_2(i)/(T^*W)$ of the first calibration substance, when the characteristic peak of the measurement spectrum line of a second calibration substance reaches the intensity value $I_2(i)$; and
calculating the constant $C=L_1 \backslash L_2$.

9. A computer readable storage medium storing one or more programs, wherein the one or more programs comprise instructions, and when being executed by a computer the instructions cause the computer to execute a mixture detection method comprising:

performing measurement spectrum line collection on a mixture consisting of different kinds of substances to identify the kinds of the substances in the mixture, wherein a solvent of the mixture is a first calibration substance;
selecting a characteristic peak of a measurement spectrum line of each kind of substance according to the kinds of the substances, and obtaining an intensity proportion of the characteristic peak of each kind of substance;
querying a relative activity database according to the kinds of the substances to obtain relative activity corresponding to each kind of substance, wherein the relative activity database comprises the relative activity L of at least one kind of standard sample substance, wherein $$L = C \sum_{i=0}^{n} L(i)/n,$$

$L(i)=I(i)/(T^*W)$, and C is a constant; and when the first calibration substance is mixed with the standard sample substance according to a first predetermined proportion, T represents an integration time when the characteristic peak of the measurement spectrum line of the standard sample substance reaches an intensity value I(i), W represents an excitation intensity of a signal source of the measurement spectrum line, and n represents collection times of the intensity value of the measurement spectrum line of the standard sample substance; and
determining the proportion contents of the different kinds of substances contained in the mixture according to the intensity proportion of the characteristic peak of each kind of substance and a quotient of the relative activities.

10. The computer readable storage medium according to claim 9, wherein when being executed by the computer the instructions further cause the computer to implement the following steps:
when the first calibration substance and the standard sample substance are mixed according to a first predetermined proportion, setting the excitation intensity W of the signal source, and setting the integration time T;
obtaining the relative activity L of the standard sample substance, when the characteristic peak of the measurement spectrum line of the standard sample substance reaches the intensity value I(i); and
adding the relative activity L of at least one standard sample substance to the relative activity database.

* * * * *